(12) United States Patent
Sethi et al.

(10) Patent No.: US 6,994,547 B1
(45) Date of Patent: Feb. 7, 2006

(54) IMPLANT ALIGNMENT

(76) Inventors: Ashok Sethi, 33 Harley Street, London W1N 1DA (GB); Peter Sochor, 125 Imperial Drive, Harrow HA 2 7 HW, Middlesex (GB)

( * ) Notice: Subject to any disclaimer, the term of this patent is extended or adjusted under 35 U.S.C. 154(b) by 114 days.

(21) Appl. No.: 10/089,102

(22) PCT Filed: Oct. 23, 2000

(86) PCT No.: PCT/GB00/04087

§ 371 (c)(1),
(2), (4) Date: Jul. 31, 2002

(87) PCT Pub. No.: WO01/28450

PCT Pub. Date: Apr. 26, 2001

(30) Foreign Application Priority Data

Oct. 21, 1999 (GB) .................................. 9924959

(51) Int. Cl.
*A61C 8/00* (2006.01)
(52) U.S. Cl. ........................................ 433/72; 433/172
(58) Field of Classification Search ................. 433/72, 433/75, 172, 173; 33/513
See application file for complete search history.

(56) References Cited

U.S. PATENT DOCUMENTS

| | | | | |
|---|---|---|---|---|
| 4,842,518 A | * | 6/1989 | Linkow et al. | 433/174 |
| 5,195,891 A | * | 3/1993 | Sulc | 433/173 |
| 5,350,301 A | * | 9/1994 | De Buck | 433/173 |
| 5,538,426 A | * | 7/1996 | Harding et al. | 433/172 |
| 5,571,015 A | * | 11/1996 | Siegmund | 433/173 |
| 5,695,334 A | * | 12/1997 | Blacklock et al. | 433/173 |
| 5,876,204 A | * | 3/1999 | Day et al. | 433/173 |
| 5,927,979 A | | 7/1999 | Misch et al. | |
| 5,947,733 A | | 9/1999 | Sutter et al. | |
| 6,273,720 B1 | * | 8/2001 | Spalten | 433/173 |

FOREIGN PATENT DOCUMENTS

JP  08/252269  10/1996

* cited by examiner

*Primary Examiner*—Ralph A. Lewis
(74) *Attorney, Agent, or Firm*—Dennison, Schultz, Dougherty & MacDonald

(57) ABSTRACT

An apparatus for alignment of dental implants in which an implant in provided with a generally axial bore and a plurality of angled templates, each adapted for operative inter-connection with the bore of the implant. Each template includes a locator lug adapted for inter-engagement with the axial bore of the implant, each lug having a circular cross-section.

7 Claims, 4 Drawing Sheets

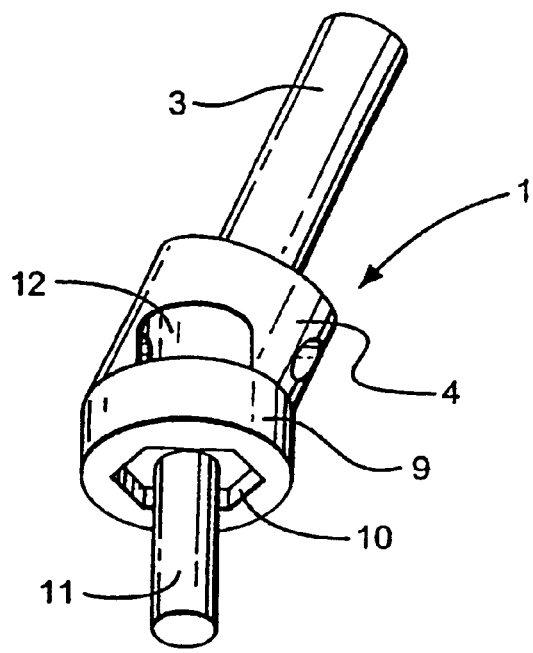
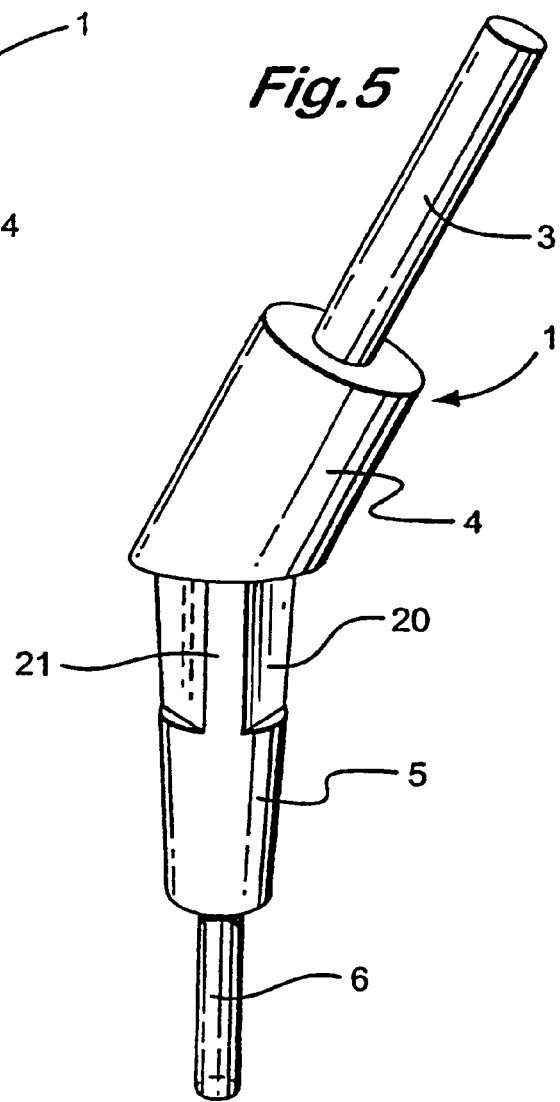

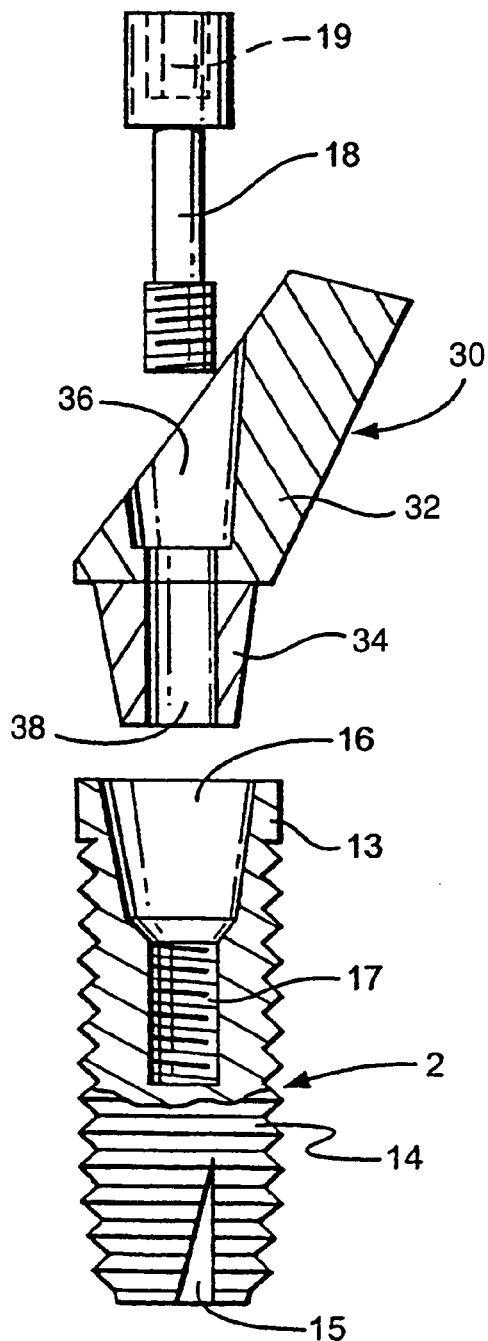
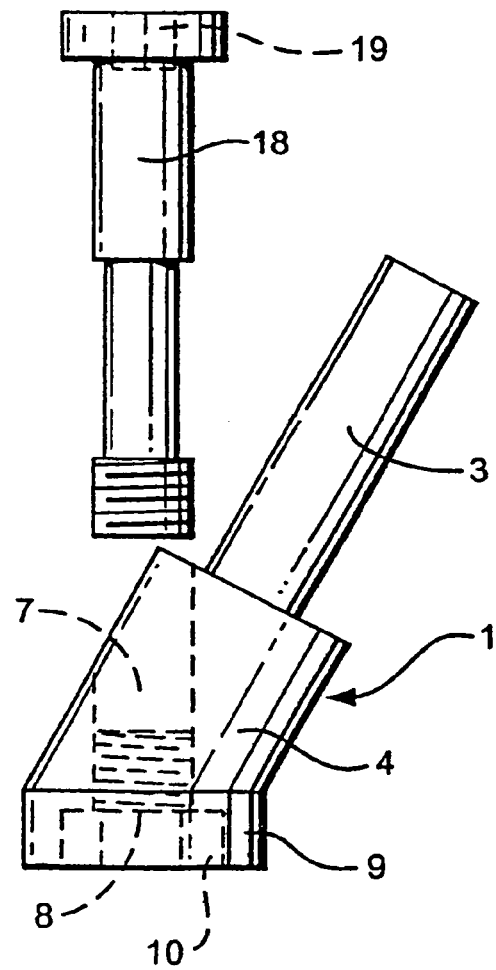

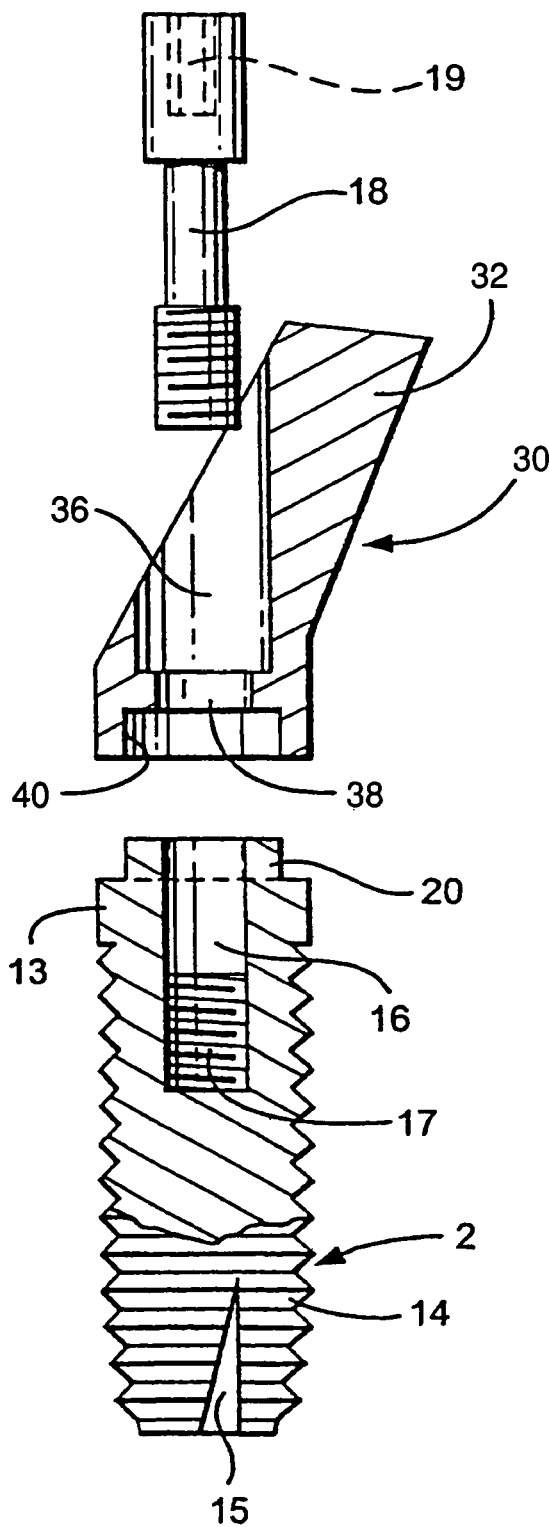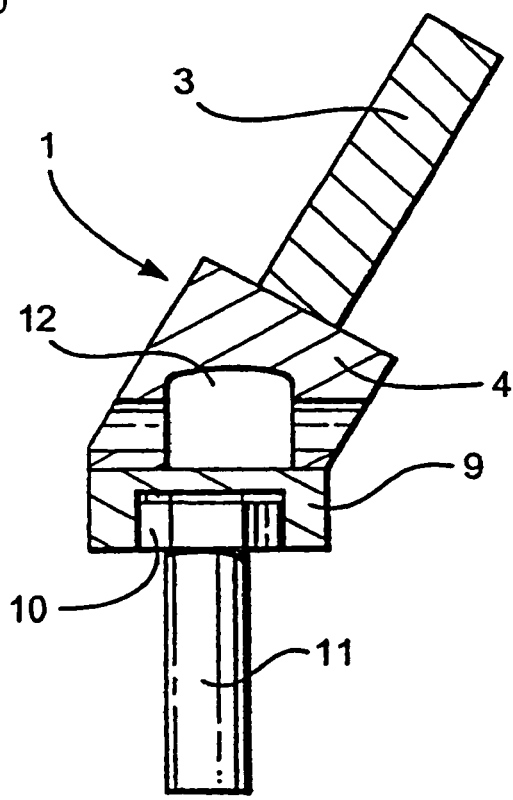

IMPLANT ALIGNMENT

The present invention relates to the alignment of dental implants and to a method for their alignment. In the Probe, September 1998, 1 have described a dental implant and a method for its insertion. In this arrangement a site is selected so that it is in the middle of a ridge. The jaw bone is drilled using internally irrigated titanium alloy burs so that it is sited between the labial and palatal cortical plates, making sure that the adjacent teeth and anatomical structures are avoided. The implant is inserted until level with the bone.

Abutment or template selection is effected by using a trial abutment (template) which measures the restorative angle, allows the implant to be positioned to the correct depth, and aligns the driving flat (or hex) in the correct plane The trial abutment (template) should fit within the hollow prosthetic envelope. This ensures that the final abutment will be in the right position. Any adjustments to the position of the implant can now be made before it is integrated. The cover screw is then replaced, the wound is sutured and the implant is allowed to integrate over a period of about six months.

The depth to which the implants are placed is important since if they are too deep this may result in bone loss (to the $1^{st}$ thread) which is not ideal, and if they are not deep enough they may become exposed prematurely. That a trial abutment or template is necessary is shown by the fact that otherwise there is no way that the angle of the abutment can be selected and the plane of orientation measured or changed unless this is done at the $1^{st}$ stage of surgery.

In order to achieve this, previously each template was provided with a downwardly depending lug provided with a plurality of driving planes for co-operation with similarly shaped receptor planes in the corresponding bore in which it was adapted to fit. Said "internal hex" arrangements can be satisfactory but give rise to a number of problems. In the first place the internal driving planes have to be small and therefore their manufacture is relatively difficult. However because they can be subjected to significant rotational forces during positioning the manufacturing tolerances must be of a low order. Most of all the utilisation of the internal driving flats, as previously suggested raises the difficulty that the dentist cannot be sure that the template is fully "home" on the implant, which can give rise to misalignments once full implant integration has occurred.

The need therefore exists for a template which will drive the implant during rotation only if the template and the implant are fully engaged. Further there is a need to ensure that the turning moment applied by the template to the implant is as positive as possible.

According to the present invention there is provided an apparatus for the alignment of a dental implant, said apparatus comprising an implant comprising a generally axial blind bore and a plurality of angled templates each adapted for operative inter-engagement with the bore of the implant; characterised in that each template comprises a locator lug for inter-engagement with the axial bore of the implant, said lug comprising a circular cross-section. It is preferred that the lug shall have a frusto-conical section for inter- engagement with a corresponding bore in the implant (or taper-lock). In a further embodiment the frustro-conical section includes a plurality, preferably four, of driving planes for co-operation with the bore of the implant. It is also preferred that the frusto-conical section terminates towards its free end in a portion of a smaller diameter.

Alternatively the locator lug may be of a right cylindrical configuration and a plurality of driving planes are provided internally of the body of the template for operative inter-connection with a corresponding set of driving flats positioned about the mouth of the bore of the implant.

In an alternative arrangement the locator lug is separate from the template and the template is formed with a bore that is adapted to be co-axial in use with that of the implant.

In a preferred embodiment the template terminates at its intended upper end remote from the lug in a shaft or peg which has a generally elongate configuration, often of a right cylindrical shape, so that whatever its rotational position it will mimic the correct angle of the existing teeth in use.

By means of the present invention the implant will only rotate to its final position when fully inter-engaged. Partial inter-engagement, and hence misalignment of the template with the implant, is thus much less likely to occur.

The invention will now be described, by way of illustration only, with reference to the accompanying drawings wherein:—

FIG. 4 shows a side view from below of another template of the invention;

FIG. 5 shows a side view a template somewhat as shown in FIG. 1 but with a plurality of driving planes disposed in frusto-conical portion.

FIG. 6 shows an exploded side view of an abutment with a frusto-conical lug in part vertical section;

FIG. 7 shows a side view in part section of a template with locking flats to form a external "hex" on the implant;

FIG. 8 shows an exploded side view in part section of an abutment and implant in accordance with FIG. 2, FIG. 9 shows a side view part section of the arrangement of FIG. 4, and Turning first to FIGS. 1 to 4, FIG. 1 shows a template (comprising a main body which is generally angled to the axis of an implant.

A template alignment shaft 3 and body 4 are angled to the axis of the implant in use by an amount varying from 5° and 45° degrees. The template and the implant are arranged such that they are correctly positionable prior to integration relative to a bore positioned in the jaw by means of the correct orientation of the shaft 3 relative to the existing teeth in use.

Figure 1:
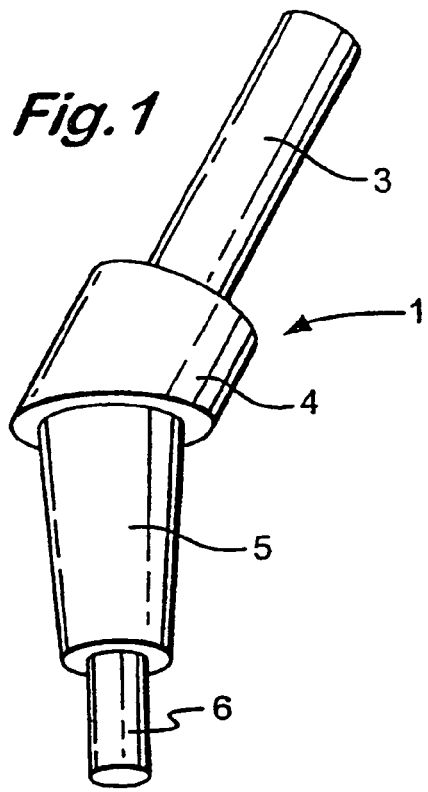
FIG. 1 shows a side view from below of a first template of the invention.
Figure 3:
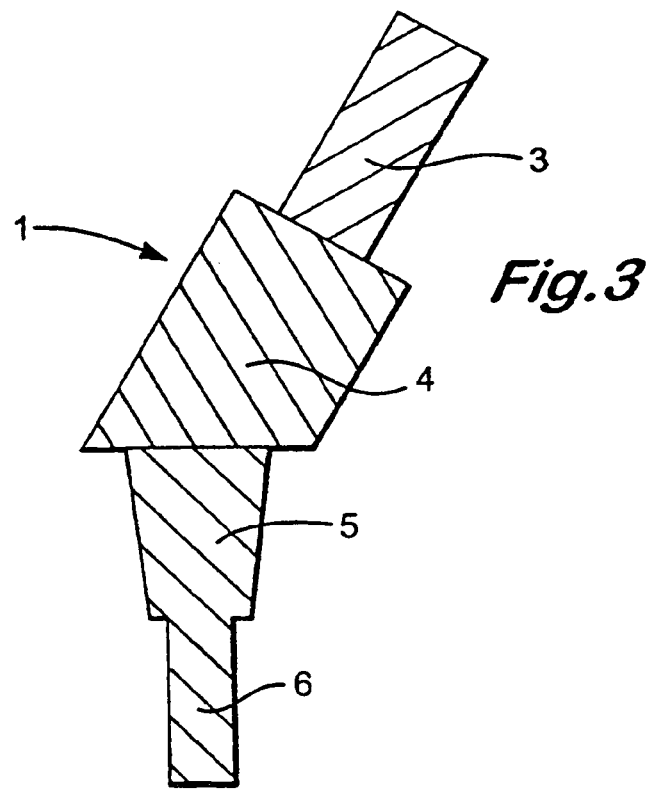
FIG. 3 shows a side view of the first template in cross-section.

As is shown in FIG. 1, the body of the template 1 terminates in generally downwardly depending frusto-conical portion 5 and a right cylindrical extension piece 6. It is arranged that frusto-conical portion 5 and the extension piece 6 are generally co-axial with the bore of the implant 2. As will be appreciated the locking force between the implant and the template is only established when they are fully inter-engaged. A similar arrangement to that shown in FIG. 1 is shown in cross-section in FIG. 3.

Figure 2:
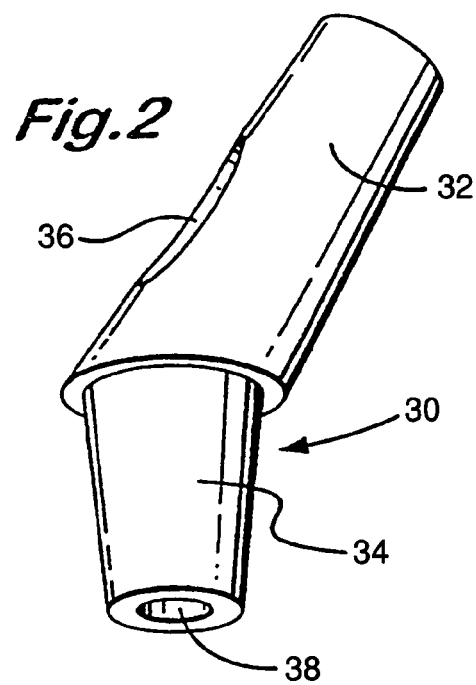
FIG. 2 shows a side view from below of a final abutment for use with the invention.

A similar arrangement is shown for an abutment 30 in FIG. 2. In this arrangement the body 32 is provided along its length with an upper most aperture 36, said aperture extending downwardly to terminate at a lower most aperture 38. A frusto-cone 34 extends at an angle to the body 32, the aperture 36 terminating in the frusto-cone. A bolt (shown generally in FIGS. 6, 7 and 8) passes through the body to locate the template on the implant as necessary. It is desirable that such a bolt should be provided with an Allen keyway for tightening purposes.

FIG. 4 provides an alignment shaft 3 similar to that shown in FIG. 1 and a body 4, again similar to that shown in FIG. 1 with the exception that in this arrangement a rotation aperture 12 is provided through the body 4 in order to locate a rotation rod therein. The arrangement of FIG. 4 also provides a downwardly depending locator lug 11 which has a circular cross-section which is in the form of a right cylinder for location in a corresponding bore in the implant.

FIG. 5 shows an arrangement similar to FIG. 1 but wherein the frusto-conical portion 5 includes a plurality of driving planes 20, but wherein the radially outer edge (21) of the planes 20 has a frusto-conical aspect so that it forms a continuous surface with the frusto-conical portion 5. This allows the template 1 to inter-engage with a co-operating axial bore while also having a positive inter-engagement therewith.

An exploded diagram of the implant and abutment assembly according to the present invention, somewhat as shown in FIG. 2, is shown in FIG. 6. In this arrangement, shown in partial cross-section, a threaded bolt 18 is provided with an Allen key aperture 19 and is adapted for location in an upper bolt aperture 36. The shaft of the bolt 18 passes through the frusto-conical portion of the abutment 30 and through the lower bolt aperture 38.

With the implant and the template fully inter-engaged, the threaded end of the bolt 18 enters a recess 16 in the implant 2. Implant 2 is provided to its exterior with a ribbed edged body 14 terminating towards its upper edge in an annular implant head 13. At its other (lower) end is a cut out 15 for reasons of bone integration.

In use the bolt 18 secured in the aperture 36 passes into the recess 16 and into the screw thread cavity 17, whereupon rotation of the Allen key in aperture 19 causes the abutment 30 to lock onto the implant 2 in a temporary fashion. The Allen key can then be used to rotate the abutment 30 into its correct orientation relative to other teeth. The bolt 18 then may be withdrawn without disturbing the implant 2 and the abutment 30 may be removed and recorded.

A similar arrangement is shown in FIG. 7 but in this instance bolt 18 is provided with standard external driving flats 18', while the template 1 is provided with internal driving flats 10 only.

In FIG. 8 there is provided an exploded arrangement showing in part section a further embodiment. Its modus operandi has been fully described with regard to FIG. 6. The only difference lies in that instead of the frusto-conical portion 34, there is provided a plurality of internal locking flats 40 for inter-engagement with an external "hex" 20 secured about the mouth of the recess 16 in the implant 2. It will be appreciated that the effect of the external hex 20 is to locate the body 32 of the abutment 30 but only when the bolt 18 is fully inter-engaged by means of the Allen key engaged in the aperture 19. Again by means of the Allen key (not shown) abutment 30 can be placed in its correct position by thereby rotating the implant 2 and subsequently removing the same.

A similar arrangement is shown in FIG. 9 which shows the arrangement of FIG. 4 in side view and in partial cross-section. The locator lug 11 is right cylindrical and acts to locate the template 1 in position in the implant 2 but of course only once fully inter-engaged. It may then be rotated once the flats 10 have been inter-engaged with the external hex 20 as shown in FIG. 8.

In the claims:

1. Apparatus for alignment of a dental prosthesis, said apparatus comprising:
    an implant for insertion in the jaw bone of a patient, the implant having a generally axial bore internally threaded over a portion of its length;
    an abutment to which the prosthesis will be formed, and which is locked to the implant by interaction of a separable bolt which is externally threaded over a portion of its length with the internal threads of the implant; and
    a plurality of angled templates for use with said implant, each of said templates being a single piece and comprising a body having a right cylindrical, locator lug at one end thereof and a right cylindrical alignment shaft at an opposite end thereof, said locator lug being constructed and arranged to interact with the axial bore of the implant only when the implant and template are fully inter-engaged, and said alignment shaft is constructed and arranged at an inclined angle to the locator lug for orientation of the alignment shaft relative to teeth adjacent the implant,
    wherein each template of said plurality of templates has a different inclined angle between 5 and 45', and one of said templates is selected to determine a correct abutment to use, the selection of said one template being made on the basis of the orientation of the alignment shaft thereof relative to the teeth adjacent the implant.

2. Apparatus according to claim 1, wherein the locator lug comprises a frusto-cone having a portion of smaller diameter towards a free end of the lug.

3. Apparatus according to claim 2, wherein the locator lug further comprises an extension piece extending generally axially from the frusto-cone towards the free end of the locator lug.

4. Apparatus according to claim 3, wherein the frusto-cone comprises a plurality of driving flats disposed on portions of its surface, constructed and arranged for interconnection with corresponding elements on the implant.

5. Apparatus according to claim 2, wherein the frusto-cone comprises a plurality of driving flats disposed on portions of its surface.

6. Apparatus according to claim 1, wherein each said template comprises a shaft remote from the locator lug, said shaft being adapted to mimic the adjacent teeth.

7. A method for alignment of a dental prosthesis, said method comprising:
    inserting an implant in the jaw bone of a patient, the implant having a generally axial bore internally threaded over a portion of its length;
    providing a plurality of angled templates for use with said implant, each of said templates comprising a body having a right cylindrical locator lug at one end thereof and a right cylindrical alignment shaft at an opposite end thereof, said locator lug being constructed and arranged to interact with the axial bore of the implant only when the implant and template are fully inter-engaged, and said alignment shaft is constructed and arranged at an inclined angle to the locator lug for orientation of the alignment shaft relative to teeth adjacent the implant, wherein each of said plurality of templates has a different inclined angle between 5° to 45°;
    selecting one of said templates on the basis of a correct orientation of the alignment shaft thereof relative to the teeth adjacent the implant; and
    selecting an abutment to which the prosthesis will be formed based on the inclined angle of the selected template, said abutment being locked to the implant by interaction of a separable bolt which is externally threaded over a portion of its length with the internal threads of the implant.

\* \* \* \* \*